(12) United States Patent
Banaei (10) Patent No.: US 8,771,967 B2
(45) Date of Patent: Jul. 8, 2014

(54) IMMUNOMODULATION OF FUNCTIONAL T CELL ASSAYS FOR DIAGNOSIS OF INFECTIOUS OR AUTOIMMUNE DISORDERS

(75) Inventor: Niaz Banaei, Palo Alto, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 118 days.

(21) Appl. No.: 13/297,818

(22) Filed: Nov. 16, 2011

(65) Prior Publication Data

US 2012/0129197 A1   May 24, 2012

Related U.S. Application Data

(60) Provisional application No. 61/414,339, filed on Nov. 16, 2010.

(51) Int. Cl.
*G01N 33/53* (2006.01)

(52) U.S. Cl.
USPC ........... 435/7.2; 435/7.1; 435/7.21; 435/7.32; 435/7.92

(58) Field of Classification Search
None
See application file for complete search history.

(56) References Cited

U.S. PATENT DOCUMENTS

| 7,608,392 B2 | 10/2009 | Rothel et al. |
| 2007/0202546 A1 | 8/2007 | Dwyer et al. |
| 2011/0212090 A1 * | 9/2011 | Pedersen et al. ........... 424/133.1 |

OTHER PUBLICATIONS

Mogensen, "Pathogen Recognition and Inflammatory Signaling in Innate Immune Defenses", Clinical Microbiology Reviews (2009), 22(2):240-273.

* cited by examiner

*Primary Examiner* — Michael Pak
(74) *Attorney, Agent, or Firm* — Bozicevic, Field & Francis LLP; Pamela J. Sherwood (57) ABSTRACT

Improved assays for detecting the presence of a specific cell-mediated immune response in an individual are provided, where a sample comprising T cells and other cells of the immune system, usually a blood sample or derivative thereof, is contacted with test antigen(s) of interest in the presence of a pattern recognition receptor (PRR) agonist. The sample is incubated for a period of time sufficient to activate effector T cells; and release of immune effector molecule(s) is then detected. In some embodiments, the PRR is an agonist of a toll-like receptor (TLR) expressed by mature antigen presenting cells, including without limitation agonists TLR3 and TLR7, such as LPS, poly I:C, imiquimod, etc.

8 Claims, 6 Drawing Sheets

IMMUNOMODULATION OF FUNCTIONAL T CELL ASSAYS FOR DIAGNOSIS OF INFECTIOUS OR AUTOIMMUNE DISORDERS

The ability to accurately diagnose infectious disease is critically important for a number of reasons; including epidemiological considerations and provision of effective therapy. Often the direct assessment of the presence of a pathogen is not possible, and diagnosis relies on detecting the presence of an immune response to the pathogen. Evidence of an immune response may be based on detection of antibodies specific for a pathogen; or for the presence of a T cell mediated response to the pathogen.

For example, the tuberculin skin test (TST) has been a widely used immunologic test for *Mycobacterium tuberculosis* infection. The method involves sub-dermal injection of antigens, followed by determination of a wheal and flare at the site of injection, indicating the presence of a cell-mediated immune response. However, the test suffers from a number of drawbacks. A valid TST requires proper administration by the Mantoux method with intradermal injection of tuberculin-purified protein derivative into the volar surface of the forearm. In addition, patients must return to a health-care provider for test reading, and inaccuracies and bias exist in reading the test. Also, false-positive TSTs can result from contact with nontuberculous mycobacteria or vaccination with Bacille Calmette-Guerin (BCG), because the TST test material contains antigens that are also in BCG, from immune boosting, and certain nontuberculous mycobacteria.

The recognition that interferon gamma (IFN-γ) plays a critical role in regulating cell-mediated immune responses has led to development of interferon gamma release assays (IGRAs) for the detection of antigens that trigger a T cell immune response. Pathogens that are characterized by a T cell mediated immune response include intracellular bacteria, such as *M. tuberculosis*; as well as viruses, certain fungi and protozoan parasites, and autoantigens.

The first IGRA approved by the FDA as an aid for diagnosing *M. tuberculosis* infection used an enzyme-linked immunosorbent assay (ELISA) to measure the amount of IFN-γ released in response to tuberculin-purified protein derivative (PPD) compared with controls. However, the specificity was less than that of TST, and new tests were developed to assess response to synthetic overlapping peptides that represent specific *M. tuberculosis* proteins present in all *M. tuberculosis*, but absent from BCG vaccine strains and from most nontuberculous mycobacteria. Because these peptides stimulate less IFN-γ release compared with PPD, a more sensitive ELISA was required to measure IFN-γ concentrations.

For IGRAs to measure IFN-γ response accurately, a fresh blood specimen that contains viable white blood cells is needed. This requirement limited the use of early IGRAs to facilities in which trained laboratorians could begin testing blood within a few hours of its collection, but was subsequently addressed by providing control materials and antigens in special tubes used to collect blood for the test, thus allowing more direct testing of fresh blood. An alternative test uses an enzyme-linked immunospot assay (ELISpot) to detect increases in the number of cells that secrete IFN-γ after stimulation with antigen.

Because of administrative and logistic difficulties associated with the TST, IGRAs are attractive diagnostic aids for detecting infection, including without limitation infection by *Mycobacterium tuberculosis*. IGRA results can be available within 24 hours without the need for a second visit. As laboratory-based assays, IGRAs are not subject to the biases and errors associated with TST placement and reading. However, errors in collecting, labeling, or transporting blood specimens, or while performing and interpreting these assays can decrease IGRA accuracy. Also, IGRAs can lack sensitivity compared to reference standard methods. The present invention addresses this issue.

Interferon gamma release assays are described, for example in U.S. Pat. No. 7,608,392; and in International Application US2007/202546.

SUMMARY OF THE INVENTION

Compositions and method are provided for improved assays for detecting the presence of a specific cell-mediated immune response in an individual. In the methods of the invention, a sample comprising T cells and other cells of the immune system, usually a blood sample or derivative thereof, is contacted with test antigen(s) of interest in the presence of a pattern recognition receptor (PRR) agonist. The sample is incubated for a period of time sufficient to activate effector T cells; and release of IFN-γ or other cytokine or immune effector molecule(s) is then detected. The presence or level of immune effector is then indicative of the level of cell mediated responsiveness of the subject. The PRR agonist is shown herein to increase the sensitivity of the assay. The methods find use, for example, in analysis of samples from individuals that typically have a low signal, including without limitation pediatric and immunocompromised individuals.

PRR agonists of interest include, without limitation, agonists of a toll-like receptor (TLR) expressed by mature antigen presenting cells, including without limitation agonists for TLR3 and TLR7, such as poly I:C, imiquimod, etc. In some embodiments a combination of PPR agonists are utilized, which combination may provide for a synergistic enhancement of signal relative to the use of a single agent. For example, a combination of poly(I:C) and Tri-DAP can be synergistic.

In some embodiments the immune effector protein is a cytokine or a non-cytokine effector, including without limitation IFN-γ, and the like. The presence or level of immune effector protein may be determined at the level of the protein itself or to the extent to which a gene is expressed. Conveniently, assays are known in the art for measuring cytokine release may find use in the methods of the invention, for example ELISA and ELISpot assays.

Test antigens of interest include any antigen that induces a cell-mediated immune response, for example antigens associated with intracellular bacteria, fungi, protozoan parasites, virus, autoantigens, etc. In some specific embodiments the test antigens are *M. tuberculosis* antigens, particularly including antigens absent from BCG vaccine strains and from most nontuberculous mycobacteria.

The present invention further provides kits comprising reagents and compartments required to perform the assay. Generally, the kit further comprises a set of instructions. The assay may also be automated or semi-automated and the automated aspects may be controlled by computer software.

BRIEF DESCRIPTION OF THE DRAWINGS

FIG. 5. Immunomodulation of Quantiferon assay with TLR ligands enhances antigen presentation. (Panel A) Analysis of the induction of cytokines in whole blood stimulated with TLR agonists. Blood was incubated in the QFT-GIT Nil tube in the absence or presence of poly(I:C) (40 μg/ml) and LPS (250 pg/ml) for 22 h. Wilcoxon's test was used to compare differences in medians (horizontal lines). *, P ≤0.05, **, P ≤0.005, (Panel B) Kinetics of IFN-γ release (TB Ag minus Nil) in the QFT-GIT assay without and with immunomodulation with poly(I:C) 40 μg/ml. (Panel C) Flow cytometry analysis of surface expression of MHC class I and II and costimulatory molecules on antigen presenting cells stimulated with TLR ligands. Whole blood incubated in the QFT-GIT Nil tube in the absence or presence of poly(I:C) (40 μg/ml) and LPS (250 pg/ml) for 3 h. (Panel D) Intracellular staining and flow cytometry of IFN-γ-producing T cells in QFT-GIT assay modulated with TLR ligands. Blood was incubated in the QFT-GIT TB Ag tube for 6 or 12 h. Data are representative of one of 6 individuals in each group.

DETAILED DESCRIPTION OF THE EMBODIMENTS

In vivo development of naive T cells to effector cells is driven by mature APCs. Maturation of APCs can be triggered through activation of pattern recognition receptors (PRR), for example through Toll-like receptors (TLRs), which sense pathogen-associated molecular patterns (PAMPs) including lipopolysaccharide (LPS) (detected by TLR4), double-stranded RNA (detected by TLR3) and single-stranded viral RNA (detected by TLR7). Stimulation of TLRs expressed by APCs leads to upregulation of MHC, costimulatory molecules, and cytokines which are essential for the development and proliferation of naive T cells to effector cells. It is shown herein that PRR agonists also enhance the response of effector T cells to antigens presented on APCs in individual with known history of infection but not in uninfected controls, for example with a commercial in-tube assay.

DEFINITIONS

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

Mammalian species that provide samples for analysis include canines; felines; equines; bovines; ovines; etc. and primates, particularly humans. Animal models, particularly small mammals, e.g. murine, lagomorpha, etc. may be used for experimental investigations. Animal models of interest include those for models of infection, autoimmunity, graft rejection, and the like.

Antigen. As used herein, antigens refer to those antigens associated with a T cell mediated response. Antigens include molecules such as nucleic acids, lipids, ribonucleoprotein complexes, protein complexes, proteins, polypeptides, peptides and naturally occurring modifications of such molecules, against which an immune response involving T cells can be generated. For each antigen, there exists a panel of epitopes that represent the immunologic determinants of that antigen. As used herein, antigens include those that are associated with autoimmune disease, infection, allergy, tissue transplant rejection, and the like. With regard to autoimmune disease, the antigens herein are often referred to as autoantigens.

Epitopes are portions of antigens that are by specific receptors on T lymphocytes. An individual antigen typically contains multiple epitopes, although there are instances in which an antigen contains a single epitope. Epitopes represent shapes recognized by immune cells, and can also be represented by non-antigen derived peptides and other molecules that possess the same epitope shape that is present within the native antigen. An example of an element with an epitope shape is an aptamer.

Antigens may include one or more whole proteins, peptides and overlapping peptides within the sequence of these proteins, and peptides representing epitopes, including immunodominant epitopes. The term polypeptide, as used herein, designates any of proteins and peptides. Where short peptides are used, preferred peptides are at least about 7 amino acids in length, may be at least about 15 amino acids in length, and as many as 22 amino acids in length. The peptides may be overlapping by 7-10 amino acids, and can encompass the whole sequence of the protein of interest. The peptide can also be a mimic of a native peptide shape, for example a cyclic peptide, nucleic acid aptamer, or can be another molecule, drug, or organic molecule that mimics the 3 dimensional shape recognized by the T cell receptor molecule.

Autoantigens are any molecule produced by the organism that can be the target of an immunologic response. In one aspect, such molecules are peptides, polypeptides, and proteins encoded within the genome of the organism. In another aspect, such molecule are post-translationally-generated modifications of these peptides, polypeptides, and proteins, such as cleavage, phosphorylation, deimination of arginine to citrulline, and other modifications generated through physiologic and non-physiologic cellular processes. In yet another aspect, such molecules include carbohydrates, lipids and other molecules produced by the organism. Examples of autoantigens include endogenous proteins or fragments thereof that elicit a pathogenic immune response. Of particular interest are autoantigens that induce a T cell mediated pathogenic response. Autoimmune diseases characterized by the involvement of T cells include multiple sclerosis, experimental autoimmune encephalitis, rheumatoid arthritis, insulin dependent diabetes mellitus, systemic lupus erythematosus, Crohns Disease, Guillain-Barre syndrome, Hashimoto's disease, temporal arteritis, ulcerative colitis, Wegener's granulomatosis, etc.

Autoimmune-associated antigens, are antigens known to be associated with, or are not currently known to be associated with but ultimately shown to be associated with, an immune-related disease. Non-limiting examples of autoimmune disease associated antigens are described below. Multiple sclerosis is associated with proteolipid protein (PLP); myelin basic protein (MBP); myelin oligodendrocyte protein (MOG); cyclic nucleotide phosphodiesterase (CNPase); myelin-associated glycoprotein (MAG), and myelin-associated oligodendrocytic basic protein (MBOP); alpha-B-crystallin (a heat shock protein); viral and bacterial mimicry peptides, e.g. influenza, herpes viruses, hepatitis B virus, etc.; OSP (oligodendrocyte specific-protein); citrulline-modified MBP (the C8 isoform of MBP in which 6 arginines have been de-imminated to citrulline), etc. Insulin dependent diabetes mellitus is associated with IA-2; IA-2beta; GAD; insulin; proinsulin; HSP; glima 38; ICA69; and p52. Rheumatoid arthritis is associated with type II collagen; hnRNP; A2/RA33; Sa; filaggrin; keratin; citrulline; cartilage proteins including gp39; collagens type I, III, IV, V, IX, XI; HSP-65/60; IgM (rheumatoid factor); RNA polymerase; cardiolipin; aldolase A; citrulline-modified filaggrin and fibrin, etc.

Infectious agents that may create a cell-mediated immune response include, without limitation, intracellular bacteria such as *Mycobacterium tuberculosis, Bartonella henselae, Coxiella bumetii, Legionella pneumophila, Brucella* species, etc. The diagnosis of *M. tuberculosis* is of particular interest. Desirably such antigens are absent in the BCG vaccine strain and other non-pathogenic mycoplasma species. Examples of such proteins include ESAT-6, CFP-10, and a series of encoded proteins disclosed in U.S. Pat. No. 7,700,118, herein specifically incorporated by reference.

Other infectious agents associated with T cell mediated immune responses include fungi, e.g. *Coccidioides immitis, Histoplasma capsulatum, Blastomyces dermatitidis*, etc.; protozoan parasites, e.g. *Toxoplasma gondii, Leishmania* species, etc.; and viruses, e.g. HIV, HTLV, JC, HSV I and II, HHV6, HHV 8, EBV, etc.

Antigens may include crude protein preparations, e.g. a cell lysate, or may comprise purified or partially purified polypeptide(s). The term substantially pure polypeptide means a polypeptide preparation which contains at most 5% by weight of other polypeptide material with which it is natively associated, and lower percentages are preferred, e.g. at most 4%, at most 3%, at most 2%, at most 1%, and at most 0.5%. It is preferred that the substantially pure polypeptide is at least 96% pure, i.e. that the polypeptide constitutes at least 96% by weight of total polypeptide material present in the preparation, and higher percentages are preferred, such as at least 97%, at least 98%, at least 99%, at least 99.25%, at least 99.5%, and at least 99.75%.

Polypeptide sequences include analogs and variants produced by recombinant methods wherein such nucleic acids and polypeptide sequences are modified by substitution, insertion, addition, and/or deletion of one or more nucleotides in the nucleic acid sequence to cause the substitution, insertion, addition, and/or deletion of one or more amino acid residues in the recombinant polypeptide.

The polypeptides may be expressed in prokaryotes or eukaryotes in accordance with conventional ways, depending upon the purpose for expression. For large scale production of the protein, a unicellular organism, such as *E. coli, B. subtilis, S. cerevisiae*, or cells of a higher organism such as vertebrates, particularly mammals, e.g. COS 7 cells, may be used as the expression host cells. Small peptides can also be synthesized in the laboratory.

The antigenic specificity of the immune system is provided by the group of proteins known as antibodies (or immunoglobulins) and T cell receptors, of which T cell receptors are of primary interest for the present invention. Through processes of genetic recombination, and in some cases somatic mutation, a very large repertoire of different protein sequences is generated in the variable regions of these proteins. The non-covalent binding interaction of these variable regions enables the immune system to bind to antigens, which are molecules such as polysaccharides, polypeptides, polynucleotides, etc. The "specificity" of a T cell receptor therefore refers to the ability of the variable region to bind with high affinity to an antigen.

The T cell receptor recognizes a more complex structure than antibodies, and requires both a major histocompatibility antigen binding pocket and an antigenic peptide to be present. The binding affinity of T cell receptors is lower than that of antibodies, and will usually be at least about $10^{-4}$ M, more usually at least about $10^{-5}$ M.

Pattern Recognition Receptors.

Pattern recognition receptors, or PRRs, are proteins expressed by cells of the innate immune system to identify pathogen-associated molecular patterns, or PAMPs, which are associated with microbial pathogens or cellular stress. They may also be referred to as pathogen recognition receptors or primitive pattern recognition receptors in light of the fact that these methods of immune surveillance have existed long before adaptive immunity evolved as an immune mechanism.

The microbe-specific molecules that are recognized by a given PRR are called PAMPs: pathogen-associated molecular patterns and include bacterial carbohydrates (e.g. lipopolysaccharide or LPS, mannose), nucleic acids (e.g. bacterial or viral DNA or RNA), bacterial peptides (flagellin, ax21), peptidoglycans and lipotechoic acids (from Gram positive bacteria), N-formylmethionine, lipoproteins and fungal glucans.

PRRs are classified according to their ligand specificity, function, localization and/or evolutionary relationships. On the basis of function, PRRs may be divided into endocytic PRRs or signaling PRRs. Signaling PRRs include the large families of membrane-bound Toll-like receptors and cytoplasmic NOD-like receptors, retinoid acid-inducible gene I-like receptors, and DNA sensors such as such AIM2. Endocytic PRRs promote the attachment, engulfment and destruction of microorganisms by phagocytes, without relaying an intracellular signal. These PRRs recognize carbohydrates and include mannose receptors of macrophages, glucan receptors present on all phagocytes and scavenger receptors that recognize charged ligands, are found on all phagocytes and mediate removal of apoptotic cells.

Toll-Like Receptors.

Recognition of extracellular or endosomal pathogen-associated molecular patterns is mediated by an array of transmembrane proteins known as toll-like receptors (TLRs). TLRs are members of the IL-1 receptor superfamily. Toll-like receptors trigger a series of mechanisms leading to the synthesis and secretion of cytokines and activation of other host defense programs that are crucial to the development of innate or adaptive immune responses. In mammals, these receptors have been assigned numbers 1 to 11 (TLR1-TLR11). Interaction of TLRs with their specific PAMP induces NF-κB signaling and MAP kinase pathway and therefore the secretion of pro-inflammatory cytokines and co-stimulatory molecules. Molecules released following TLR activation signal to other cells of the immune system making TLRs key elements of innate immunity and adaptive immunity.

Microbial-derived TLR ligands include a wide range of molecules with strong adjuvant activity that can activate DCs, macrophages and other APCs. TLRs are involved in the pathogenesis of autoimmune disorders, and endogenous ligands also activate these receptors. As a non-limiting example, exposure to TLR3, TLR7/8 and TLR9 agonists is of interest in the methods of the present invention.

TLR agonists of interest include, without limitation, LPS and lipoteichoic acid (all recognized by TLR4); peptidoglycans (cell walls), lipoproteins (bacterial capsules) and zymosan (all recognized by TLR2 following heterodimerization with TLR1 or TLR6); flagellin (in bacterial flagella, recognized by TLR5), unmethylated bacterial or viral CpG DNA (recognized by TLR9) and viral RNA (single-stranded recognized by TLR7 and TLR8, double-stranded by TLR3); fungal polysaccharides, muramic acid (a bacterial cell wall peptidoglycan), bacterial DNA, schistosomal phosphatidylserine, monophosphoryl lipid A (MPL), poly I:C, imiquimod, etc.

Cytokines.

Cytokines are messenger molecules produced by B cells, T cells, macrophage, dendritic cells and other immune and host cells. For the purposes of the present invention, cytokines produced by T cells in response to antigenic stimulation are of particular interest. Cytokines include, but are not limited to IFN-γ, TNFα, IL-1a, IL-1b, IL-2, IL-3, IL-4, IL-5, IL-6, IL-7, IL-8, IL-10, IL-11, IL-12p40, IL-12p70, IL-13, IL-15, IL-17, IL-18, IL-23, TGFβ, etc. Release of IFNγ is of particular interest.

METHODS OF THE INVENTION

The methods of the invention provide improved assays for detecting the presence of a specific cell-mediated immune response in an individual. In the methods of the invention, a sample comprising T cells and other cells of the immune system, usually a blood sample or derivative thereof, is contacted with test antigen(s) of interest in the presence of a pattern recognition receptor (PRR) agonist. The sample is incubated for a period of time sufficient to activate effector T cells; and release of IFN-γ or other cytokine or immune effector molecule(s) is then detected. The presence or level of immune effector is then indicative of the level of cell mediated responsiveness of the subject.

A sample is obtained from an individual, usually a mammal as previously defined, suspected of having a cell-mediated immune response. Samples, as used herein, typically refer to a cellular sample comprising at least T cells and antigen-presenting cells, e.g. dendritic cells, monocytes, B cells, etc. Blood samples are conveniently used as a source of complex cell populations, although for certain purposes other cellular samples may find use, e.g. synovial fluid, cerebrospinal fluid, bronchial washes, tissue samples, and the like. The term blood samples may also refer to a mononuclear cell fraction, e.g. PBMC, which may be isolated by conventional methods. The patient sample may be used directly, or diluted as appropriate. Assays may be performed in any suitable physiological buffer, e.g. PBS, normal saline, HBSS, dPBS, etc., and may further contain a sugar, e.g. dextrose, heparin, etc., as known in the art.

The sample collected from the subject is usually deposited into a blood collection tube. A blood collection tube includes a blood draw tube or other similar vessel. Conveniently, when the sample is whole blood, the blood collection tube is heparinized. Alternatively, heparin is added to the tube after the blood is collected. Notwithstanding that whole blood is the preferred and most convenient sample, the present invention extends to other samples containing immune cells such as lymph fluid, cerebral fluid, tissue fluid and respiratory fluid including nasal and pulmonary fluid.

The cellular sample is incubated with a target antigen or antigens, in the presence of a PRR agonist, e.g. a TLR agonist as previously defined. The antigen and/or PRR agonist may be provided in the collection tube, or may be added to samples following collection. In addition a positive mitogen control and a negative control is included in each assay. The agonist concentrations will vary with the specific agonist being used, but will generally be sufficient to provide an effect comparable to those set forth below.

Specifically, for Poly I:C-LMW (agonist for TLR3) the agonist will usually be present at a concentration of at least about 1 μg/ml, at least about 10 μg/ml, at least about 20 μg/ml, at least about 50 μg/ml, and not more than about 250 μg/ml, or not more than about 100 μg/ml. For LPS (agonist for TLR4) the agonist will usually be present at a concentration of at least about 0.1 ng/ml, at least about 1 ng/ml, at least about 10 ng/ml, and not more than about 100 ng/ml, or not more than about 50 ng/ml. For Imiquimod (agonist for TLR7) the agonist will usually be present at a concentration of at least about 0.1 μg/ml, at least about 0.5 μg/ml, at least about 1 μg/ml, at least about 5 μg/ml, and not more than about 50 μg/ml, or not more than about 25 μg/ml. In the presence of these agonists, the T cell responses to target antigens in whole blood on average increased 10 fold in subjects known to have latent tuberculosis infections.

The incubation step may be from 5 to 50 hours, more preferably 5 to 40 hours and even more preferably 8 to 24 hours or a time period in between.

Immune cells tend to lose the capacity to mount a CMI response in whole blood after extended periods following blood draw from the subject, and responses without intervention are often severely reduced or absent 24 hours following blood draw. However, once antigen stimulation is complete, the requirement for fresh and active cells no longer exists, as the cytokines or immune effector molecules are stable in plasma and, thus, the sample can be stored, or shipped without special conditions or rapid time requirements in a similar fashion to standard serum samples used for other infectious disease or other disease diagnosis.

Following incubation of the cellular sample with antigen and PRR agonist, the release of immune effector molecules, e.g. IFN-γ, etc., may be measured by any convenient method. Methods of interest include ELISA or other assay for quantitating the concentration of release effector molecule in the sample buffer.

For example, a first antibody having specificity for the immune effector molecule of interest is either covalently or passively bound to a solid surface. The solid surface is typically glass or a polymer, the most commonly used polymers being cellulose, polyacrylamide, nylon, polystyrene, polyvinyl chloride or polypropylene. The solid supports may be in the form of tubes, beads, spheres, discs of microplates, or any other surface suitable for conducting an immunoassay. The binding processes are well known in the art and generally consist of cross-linking covalently binding or physically adsorbing, the polymer-antibody complex is washed in preparation for the test sample. An aliquot of the sample to be tested is then added to the solid phase complex and incubated for a period of time sufficient (e.g. 2-120 minutes or where more convenient, overnight) and under suitable conditions (e.g. for about 20° C. to about 40° C.) to allow binding of any molecule present in the antibody. Following the incubation period, the antibody solid phase is washed and dried and incubated with a second antibody specific for a portion of the antigen, or for the first antibody. The second antibody is usually linked to a reporter molecule which is used to indicate binding.

Both polyclonal and monoclonal antibodies are obtainable by immunization with the immune effectors or antigenic fragments thereof and either type is utilizable for immunoassays. The methods of obtaining both types of sera are well known in the art. Polyclonal sera are less preferred but are relatively easily prepared by injection of a suitable laboratory animal with an effective amount of the immune effector, or antigenic part thereof, collecting serum from the animal and isolating specific sera by any of the known immunoadsorbent techniques. The use of monoclonal antibodies in an immunoassay is particularly preferred because of the ability to produce them in large quantities and the homogeneity of the product. The preparation of hybridoma cell lines for monoclonal antibody production derived by fusing an immortal cell line and lymphocytes sensitized against the immunogenic preparation can be done by techniques which are well known to those who are skilled in the art.

In some cases, a competitive assay will be used. In addition to the patient sample, a competitor to the antibody is added to the reaction mix. The competitor and the antibody compete for binding to the polypeptide. Usually, the competitor molecule will be labeled and detected as previously described, where the amount of competitor binding will be proportional to the amount of Immune present. The concentration of competitor molecule will be from about 10 times the maximum anticipated Immune concentration to about equal concentration in order to make the most sensitive and linear range of detection.

A reporter molecule provides an analytically identifiable signal that allows the detection of antigen-bound antibody. Detection may be either qualitative or quantitative. The most commonly used reporter molecules in this type of assay are either enzymes, fluorophores or radionuclide containing molecules (i.e. radioisotopes) and chemiluminescent molecules. In the case of an enzyme immunoassay, an enzyme is conjugated to the second antibody, generally by means of glutaraldehyde or periodate. As will be readily recognized, however, a wide variety of different conjugation techniques exist, which are readily available to the skilled artisan. Commonly used enzymes include horseradish peroxidase, glucose oxidase, beta-galactosidase and alkaline phosphatase, amongst others. The substrates to be used with the specific enzymes are generally chosen for the production, upon hydrolysis by the corresponding enzyme, of a detectable colour change. Examples of suitable enzymes include alkaline phosphatase and peroxidase. It is also possible to employ fluorogenic substrates, which yield a fluorescent product rather than the chromogenic substrates noted above. In all cases, the enzyme-labeled antibody is added to the first antibody-antigen complex, allowed to bind, and then the excess reagent is washed away. A solution containing the appropriate substrate is then added to the complex of antibody-antigen-antibody. The substrate will react with the enzyme linked to the second antibody, giving a qualitative visual signal, which may be further quantitated, usually spectrophotometrically, to give an indication of the amount of antigen which was present in the sample.

There are many variations to this assay. One particularly useful variation is a simultaneous assay where all or many of the components are admixed substantially simultaneously.

An alternative method utilizes a filter immunoplaque assay, otherwise called the enzyme-linked immunospot assay (ELISPOT). These assays take advantage of the relatively high concentration of a given cell product (such as a cytokine) in the environment immediately surrounding the protein-secreting cell. These cell products are captured and detected using high-affinity antibodies. The ELISPOT assay is reviewed in "Current Protocols in Immunology, Unit 6.19, pages 6.19. 1-8".

The ELISPOT assay involves coating a purified cytokine-specific antibody to a membrane-backed microtiter plate; blocking the plate to prevent non-specific absorption of any other proteins; incubating the cytokine-secreting cells with appropriate reagents; removal of cells and reagents; adding a labeled second anti-cytokine antibody; and detecting the antibody-cytokine complex on the membrane. The ELISPOT assay thus utilizes two high-affinity cytokine-specific antibodies directed against different epitopes on the same cytokine molecule: either two monoclonal antibodies or a combination of one monoclonal antibody and one polyvalent antiserum. ELISPOT generates spots based on a colorimetric reaction that detects the cytokine secreted by a single cell. The spot represents a "footprint" of the original cytokine-producing cell. Spots are permanent and can be quantified visually, microscopically or electronically. Detection methods using fluorescence labels are also practiced in the art. The ELISPOT assay can be used in a clinical setting, where for example, each kit is able to assay 24 patient samples at one time (using 4 wells per sample in a 96 well plate).

The use of blood collection tubes is compatible with standard automated laboratory systems and these are amenable to analysis in large-scale and random access sampling. Blood collection tubes also minimize handling costs and reduce laboratory exposure to whole blood and plasma and, hence, reduce the risk of laboratory personnel from contracting a pathogenic agent such as HIV or hepatitis B virus (HBV).

The present invention further contemplates a kit for assessing a subject's capacity to mount a cell mediated response. The kit is conveniently in compartmental form with one or more compartments adapted to receive a sample from a subject such as whole blood. That compartment or another compartment may also be adapted to contain heparin where the sample is whole blood with or without a simple sugar such as dextrose. The simple sugar may also be maintained in a separate container. The kit will generally include an effective dose of at least one PRR agonist, and may frequently include a test antigen(s) of interest.

Generally, the kit is in a form which is packaged for sale with a set of instructions. The instructions would generally be in the form of a method for measuring a CMI response in a subject, said method comprising collecting a sample from said subject wherein said sample comprises cells of the immune system which are capable of producing immune effector molecules following stimulation by an antigen in the presence of a PRR agonist, incubating said sample with an antigen and then measuring the presence or elevation in level of an immune effector molecule wherein the presence or level of said immune effector molecule is indicative of the capacity of said subject to mount a cell-mediated immune response.

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

EXPERIMENTAL

Current IGRAs lack sensitivity for the diagnosis of latent or active tuberculosis. As shown herein PAMPs may increase the sensitivity of IGRAs for this purpose. Current IGRAs also lack reproducibility when subjects are serially tests over time. In this case, PAMPs may improve the reproducibility of IGRAs.

Figure 1:
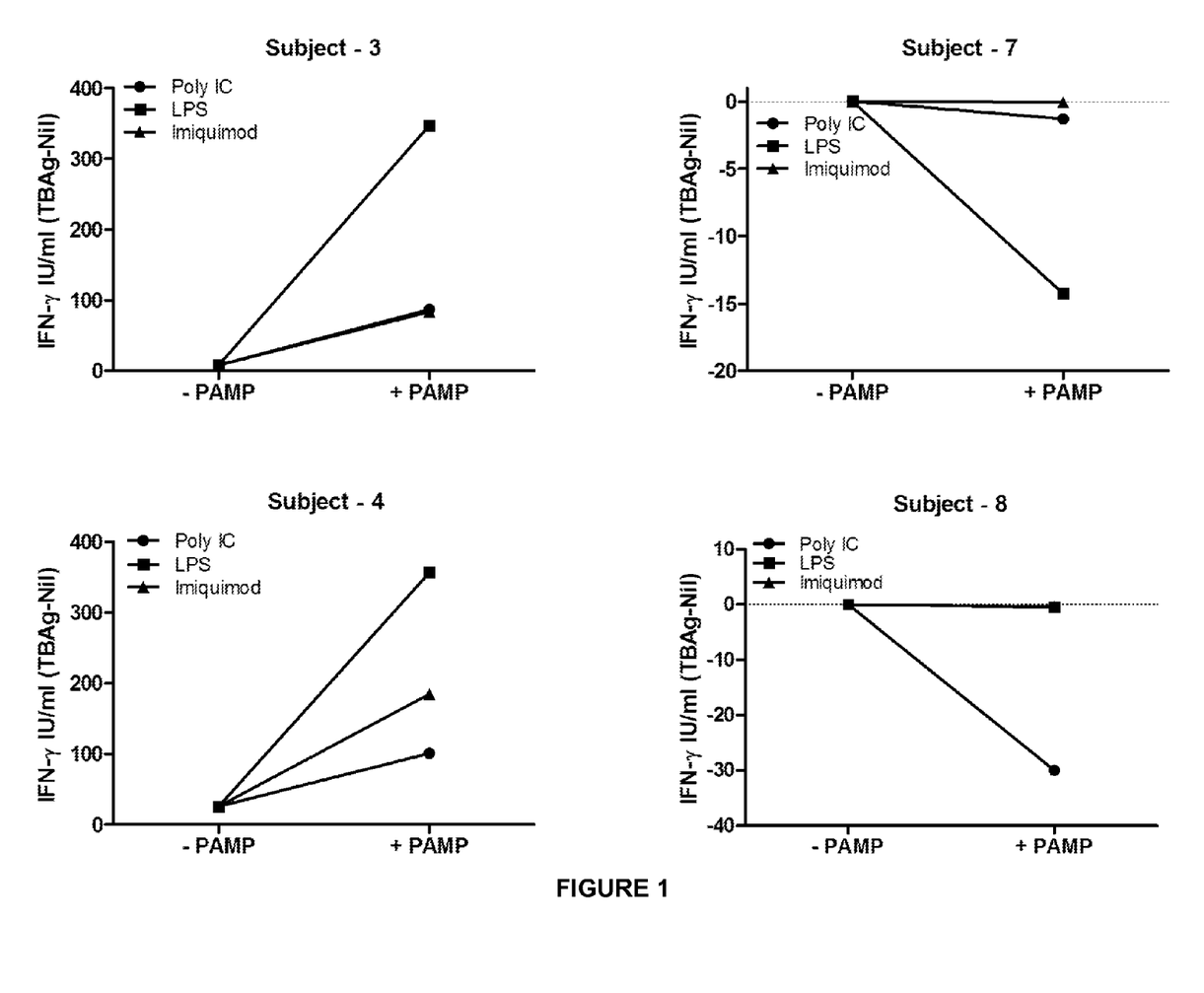
FIG. 1. PAMPs increase sensitivity of QFT-IT in LTBI.
Figure 2:
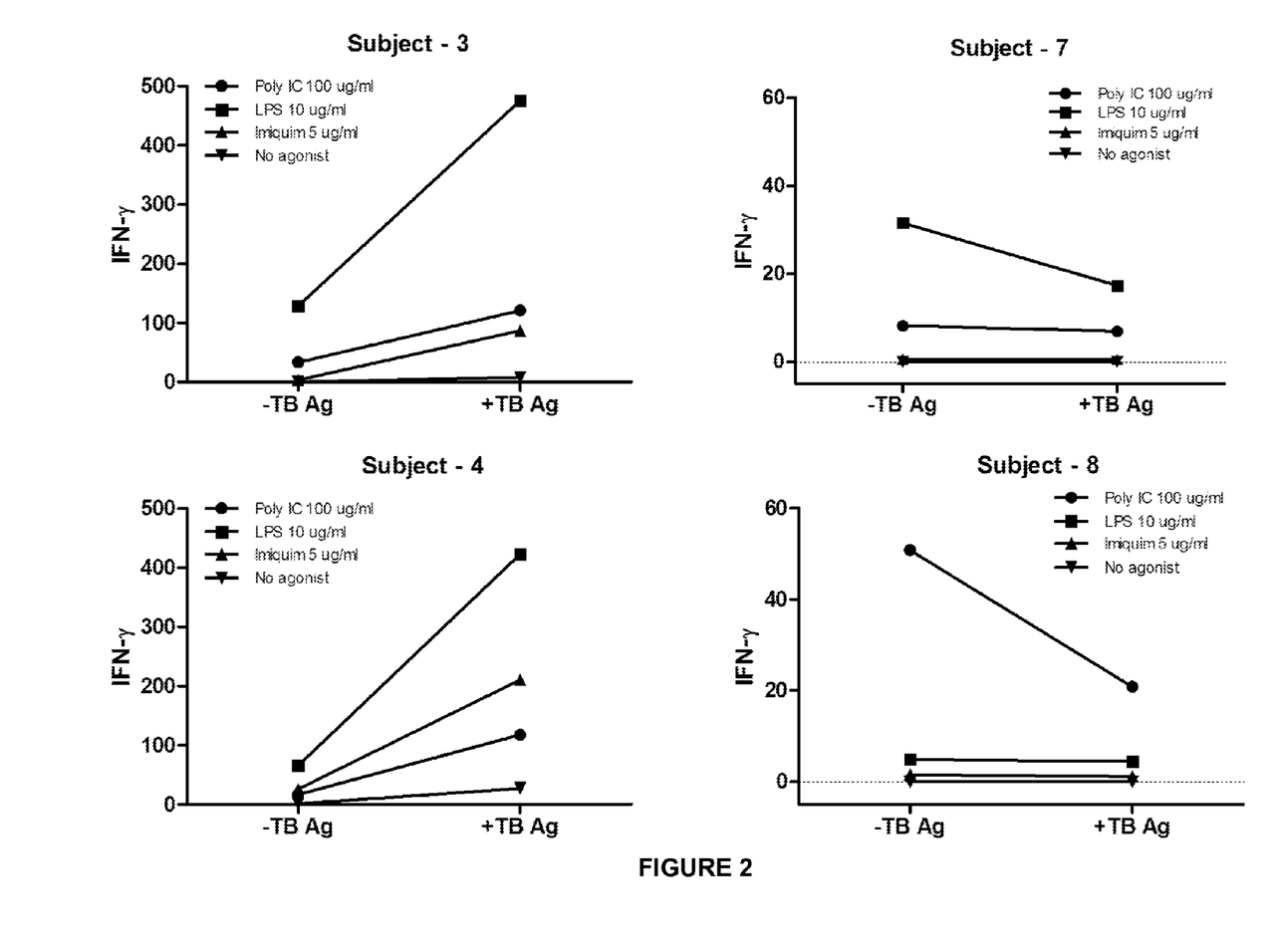
FIG. 2. Enhancement of QFT with PAMPS is Ag dependent.

An assay for cell mediated immune response was performed using the Cellestis Quantiferon gold in-tube assay according to the manufacturer's instructions, except for the addition of the PRR agonists, as shown in FIG. 1 and FIG. 2, at concentrations ranging from 10 to 100 μg/ml for Poly I:C-LMW (agonist for TLR3), 1 to 10 ng/ml for LPS (agonist for TLR4), and 1 to 5 μg/ml for Imiquimod (agonist for TLR7). One ml of whole blood or its cellular component is incubated with target antigen or antigens, in the presence of one or more PRR agonists. A negative control and a mitogen control is included in each assay. Incubation takes place at 37° C. for 16 to 24 hours. The concentration of IFN-γ is then measured with an ELISA and IFN-γ levels are interpreted using predefined cutoffs. In the presence of these agonists, the T cell responses to target antigens in whole blood on average increased 10 fold in subjects known to have latent tuberculosis infections. In the presence of these agonists, the T cell responses to target antigens in whole blood on average increased 10 fold in subjects known to have latent tuberculosis infections "but not in uninfected individuals."

Example 2

In Vitro Immunomodulation Enhances the Sensitivity of Whole Blood IFN-γ Release Assay for Diagnosis of Latent Tuberculosis Infection Given the need for novel approaches to improve the sensitivity of immunodiagnostics for diagnosis of latent *Mycobacterium tuberculosis* infection, we show that in vitro immunomodulation of whole blood interferon gamma release assay with Toll-like receptor agonists enhanced the response of T cells to *M. tuberculosis* antigens in subjects with latent infection and infected individuals who otherwise do not respond to stimulation with antigens alone.

Activation of innate immunity via pathogen recognition receptors (PRR) modulates adaptive immune responses. PRR ligands are being exploited as vaccine adjuvants and as therapeutics, but their utility in diagnostics has not been explored. Interferon-gamma (IFN-γ) release assays (IGRAs) are functional T cell assays used to diagnose latent tuberculosis infection (LTBI); however, novel approaches are needed to improve their sensitivity. Here we show that in vitro immunomodulation of a whole blood IGRA (QuantiFERON®-TB GOLD In-Tube) with Toll-like receptor agonists such as poly (I:C), LPS, and imiquimod significantly enhanced the response of T cells stimulated with *M. tuberculosis* antigens in subjects with LTBI but not in healthy controls. Immunomodulation of IGRA revealed T cell responses in subjects with LTBI who otherwise do not respond to in vitro stimulation with antigens alone. Immunomodulation of whole blood IGRA induced secretion of inflammatory cytokines and IFN-α and enhanced the surface expression of antigen presenting and costimulatory molecules on antigen presenting cells. These events correlated with an earlier and more robust release of IFN-γ. These findings identify in vitro immunomodulation of IGRAs as a novel strategy for enhancing the interrogation of T cells for diagnosis of LTBI.

Diagnosis of LTBI is made through measuring cell-mediated immune responses to *M. tuberculosis* antigens. The tuberculin skin test (TST) has served this purpose for more than a century but it lacks specificity due to cross reaction with the *M. bovis* BCG vaccine and environmental mycobacteria. More recently, the interferon-gamma (IFN-γ) release assays (IGRAs) were developed for in vitro diagnosis of LTBI. IGRAs measure IFN-γ released from antigen-specific T cells upon stimulation with *M. tuberculosis*-specific antigens thus eliminating cross reaction with BCG. Commercial IGRAs such as the QuantiFERON®-TB GOLD In-Tube (QFT) assay measure the difference in readout between antigen stimulation and the background and interpret results based on a predefined cut-off value (Cellestis Ltd, Melbourne, AUS). IGRAs are attractive alternatives to TST for their improved specificity, pre- and post-analytical standardization, and logistical advantages. However, similar to TST, they lack sensitivity for detection of latent (40% to 100%) or active (83% to 90%) infection. The sensitivity of IGRAs is further compromised in high risk groups such as HIV infected individuals, immunocompromised hosts, and children. In addition, IGRAs lack reproducibility in cohorts undergoing serialized testing, with in-subject variability ranging from 16 to 80%.

The poor performance of IGRAs is in part due to the low assay cut-off values, close to the detection limit of IFN-γ. Attempts to improve the sensitivity of IGRAs have focused on addition of novel T cell antigens or simultaneous measurement of IFN-γ and biomarkers downstream of IFN-γ signaling pathway. These modifications have yielded marginal improvements and novel approaches are needed to enhance the sensitivity and reproducibility of IGRAs.

Pathogen-associated molecular patterns (PAMP) are conserved microbial products with immunomodulatory properties. During infection, PAMPs are recognized by the innate immune cells via several families of pathogen recognition receptors (PRR) of which the Toll-like receptor (TLR) family is best characterized. Activation of pathogen sensors triggers intracellular signaling pathways which culminate in the release of inflammatory cytokines such as interleukin 6 (IL-6) and 12 (IL-12) and type I interferons (IFN-α/β). These mediators in turn stimulate the maturation of antigen presenting cells and initiation of adaptive immune responses such as the development and proliferation of antigen-specific effector T cell subsets. In the case of intracellular pathogens, effector T cells egress from lymph nodes and migrate to the site infection where they activate infected macrophages via IFN-γ.

In this report we investigated whether in vitro immunomodulation with TLR agonists can be utilized to improve the response of T cells in IGRA for diagnosis of TB infection. We show that immunomodulation of whole blood QFT-GIT assay with TLR agonists enhanced the response *M. tuberculosis*-specific T cells and that this modulation was sufficient to elicit an IFN-γ response in anergic individuals with LTBI.

Materials and Methods

Study Subjects.

Healthy adults were recruited from the Stanford Hospital clinical laboratories using a protocol approved by the Institutional Review Board. After obtaining in informed consent, volunteers were asked to complete a standardized questionnaire to assess risk factors for TB exposure. LTBI was defined as prior history of positive TST and QFT-GIT and ≥1 risk factor for LTBI. Uninfected control was defined as US born with prior negative TST and QFT-GIT and no risk factors.

Reagents.

PRR ligands were purchased from InvivoGen (San Diego, Calif.). IL-6 and IL-12 were purchased from R&D System (Minneapolis, Minn., USA) and INF-α was purchased from PBL Interferon Source (Piscataway, N.J., USA). All compounds were reconstituted in endotoxin-free water and stored at −70° C.

QuantiFERON-TB Gold In-Tube Assay.

The QFT-GIT assay was performed according to package insert with a slight modification described below. Up to 10 μA of each TLR agonist or an equivalent volume of endotoxin-free water was added to each QFT-GIT tube. Blood was collected in a 10 mL Kendall Monoject Green Stopper tube and 1 mL was quickly transferred to each QFT-GIT tube. Tubes were placed in a 3TC incubator for 22 hours or as indicated. ELISA was performed according to package insert. The remaining plasma was stored at −70° C. Calculation of IFN-γ concentrations was done with the software provided by the manufacturer. For the standard assay, a positive result was defined as TB Ag minus Nil value of ≥0.35 IU/ml.

Cytokine Profiling Assay.

Was performed at the Human Immune Monitoring Center (HIMC) at Stanford University. 100 μl of plasma from the QFT-GIT Nil tube was subjected to cytokine profiling. Procarta Cytokine Assay custom 51-plex kit (Affymetrix, Palo Alto, Calif.) was used according to manufacturer's recommendations.

Flow Cytometry.

The QFT-GIT tubes were incubated upside down to prevent migration of cells into the gel layer. At the end of incubation 100 μl of 20 mM EDTA was added per tube. Samples were vortexed and incubated at room temperature for 15 minutes. Blood was transferred to a 15 ml polypropylene tube containing 9 ml of 1×FACS™ Lysing Solution (BD Biosciences, Immunocytometry Systems, San Jose, Calif.). Samples were incubated at room temperature for 10 minutes and directly transferred to a −70° C. freezer for storage. The cell surface immune profiling studies were performed at the HIMC. The cells were thawed in warm media, washed once with FACS buffer (PBS supplemented with 2% FBS and 0.1% sodium azide) and resuspended at $1 \times 10^7$ viable cells/ml. $5 \times 10^5$ cells per well were stained for 45 min at room temperature with the following antibodies: All reagents were purchased from BD Biosciences. Cells were washed three times with FACS buffer, and resuspended in 200 FACS buffer. 10,000 cells per sample were collected using DIVA 6.0 software on an LSR11 flow cytometer (BD Biosciences). Data analysis was performed using FlowJo v9.3 by gating on live cells based on forward versus side scatter profiles, then on singlets using forward scatter area versus height, followed by cell subset-specific gating.

Statistical Analysis.

Statistical analyses were performed using the Prism software (Graph Pad, San Diego, Calif.). The Wilcoxon's test of medians was used to compare differences in medians. All statistical tests were computed for a two-sided type I error rate of 5%.

Results

Figure 3:
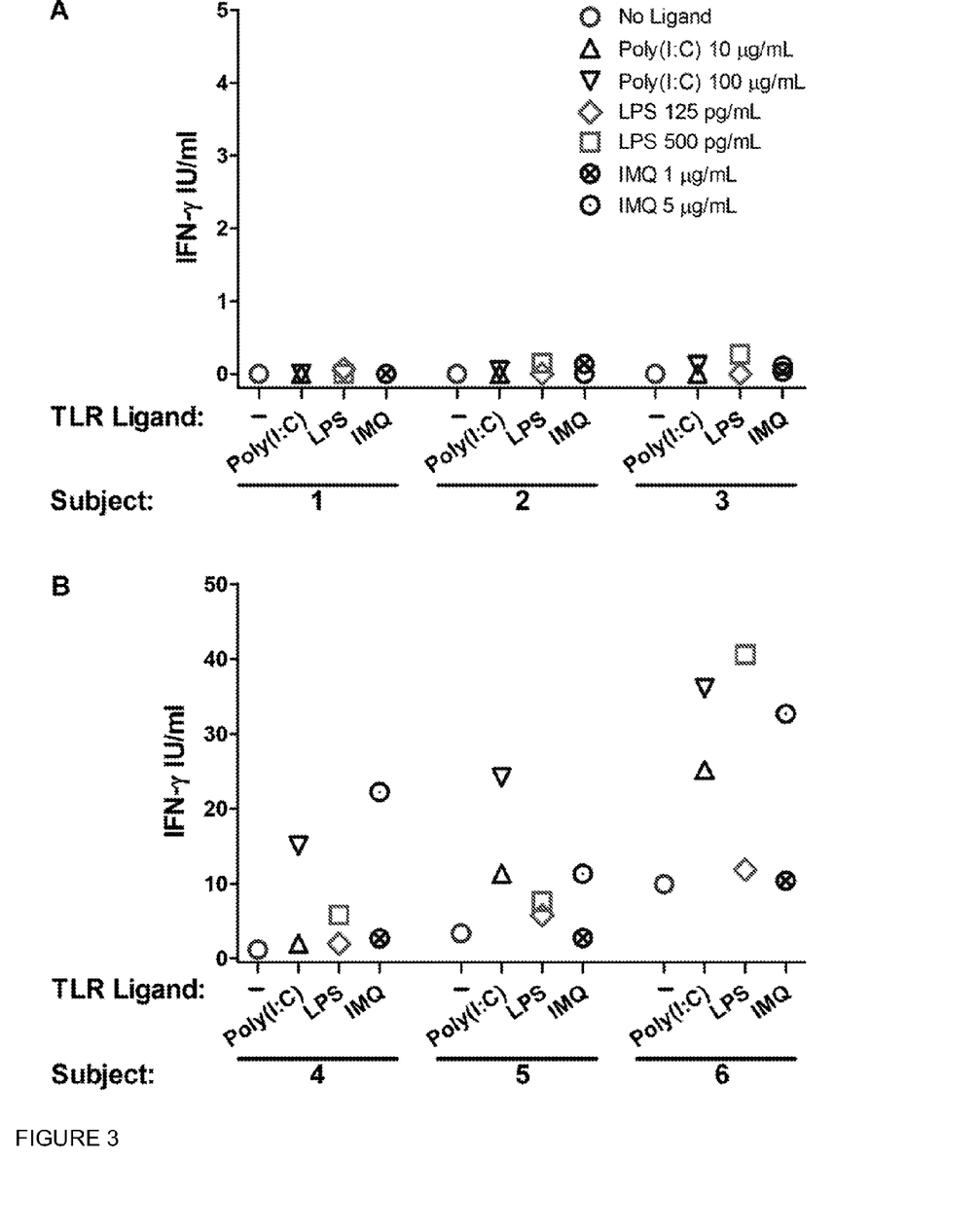
FIG. 3. Immunomodulation of Quantiferon assay enhances the IFN-γ response in subjects with LTBI. Typical IFN-γ responses (TB Ag minus Nil) for individuals with LTBI (Panel B) and uninfected controls (Panel A). Each individual was tested with the QFT-GIT assay in the absence or presence of two concentrations of poly(I:C), LPS, and imiquimod (IMQ). Data are representative of three of eight individuals in each group.
Figure 4:
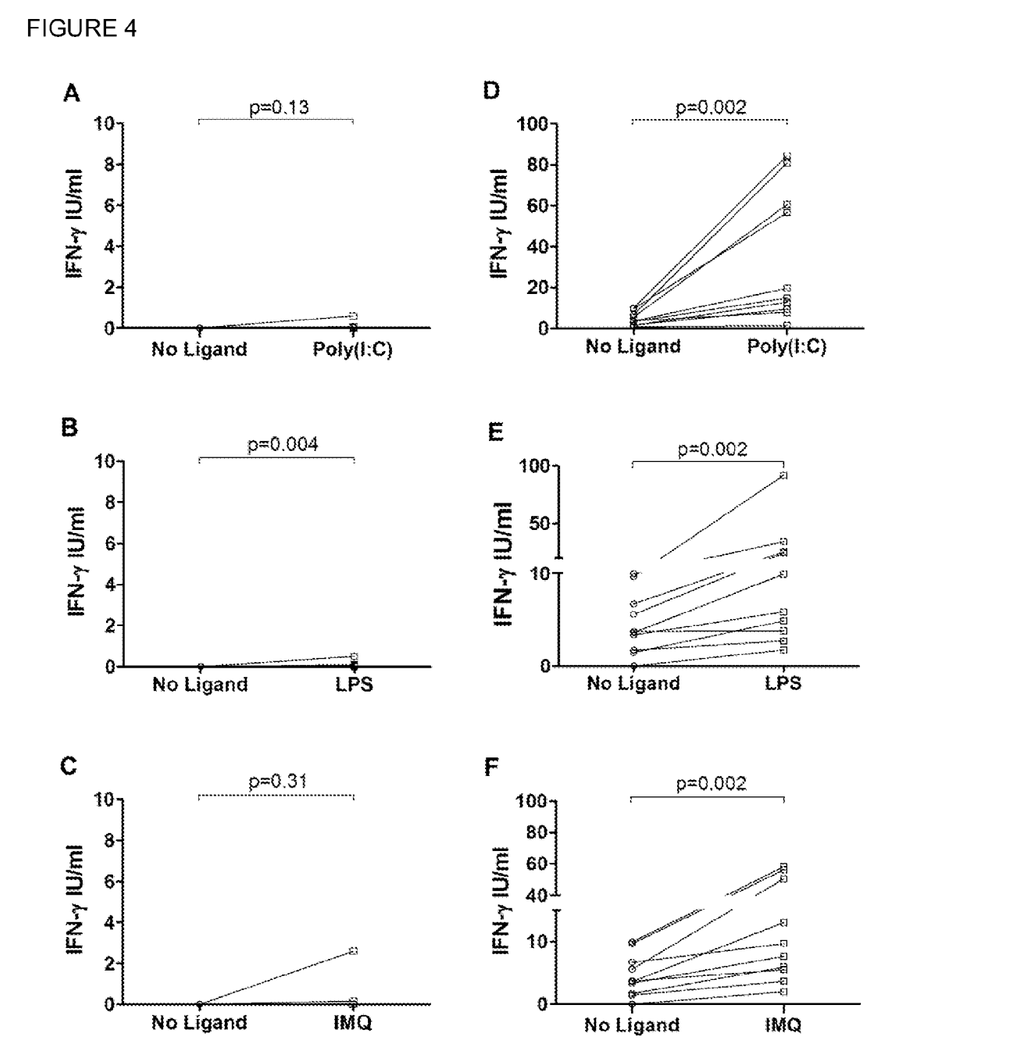
FIG. 4. Immunomodulation of Quantiferon assay enhances the IFN-γ response in subjects with LTBI. IFN-γ responses (TB Ag minus Nil) for ten individuals with LTBI (Panel D-F) and ten uninfected controls (Panel A-C). Each individual was tested with the QFT-GIT assay in the absence or presence of poly(I:C) 40 μg/ml (Panel A,D); LPS 250 pg/ml (Panel B,E), and imiquimod (IMQ) 2 μg/ml (Panel C,F). Wilcoxon's test was used to compare differences in medians.

TLR agonists enhance IFN-γ response in whole blood IGRA. To test whether immunomodulation of whole blood IGRA with PRR ligands can enhance the response of *M. tuberculosis*-specific T cells, QFT-GIT assay was performed in 8 individuals with LTBI and 8 uninfected controls in the absence and presence of TLR agonists poly(I:C), LPS, and imiquimod. These agonists were chosen because their TLRs (TLR3, TLR4, and TLR7, respectively) are differentially expressed by antigen presenting cell subsets in the peripheral blood and because intracellular signaling through these T helper 1-polarizing TLRs spans the signaling pathways downstream of all TLRs. Compared to the standard assay, modulation of QFT-GIT with poly(I:C) (10 and 100 μg/ml), LPS (125 and 500 pg/ml), and imiquimod (1 and 5 μg/ml) resulted in a dose-dependent enhancement of IFN-γ response in subjects with LTBI but not in the uninfected controls (FIG. 3). At higher concentrations, modulation of the QFT-GIT assay by TLR agonists acted in a nonspecific manner and elicited a response in uninfected controls. Testing of additional 20 individuals with an intermediate concentration of poly(I:C) (40 μg/ml), LPS (250 pg/ml), and imiquimod (2 μg/ml) showed a significant enhancement of IFN-γ response in subjects with LTBI but not in the uninfected controls (FIG. 4). Although LPS significantly increased the IFN-γ response in uninfected controls, the magnitude of the responses remained low and did not exceed 0.5 IU/ml (FIG. 4). Overall, the effect of immunomodulation on IGRA with each ligand was heterogeneous across infected subjects with each individual responding variably to the same stimulus. The enhancement of IFN-γ response ranged from 1.6 to 12.1 fold (median 5.7) with poly(I:C), 1 to 9.5 fold (median 3.1) with LPS, and 1.4 to 9.1 fold (median 3) with imiquimod. There was also variability in the magnitude of enhancement of QFT-GIT when immunomodulation was repeated in the same individual on two different occasions. Further, we investigated for synergy between PAMPs based on work in mice showing synergistic action between TLRs and Nod-like receptor family member, Nod1, in generation of adaptive immune responses. Immunomodulation of QFT-GIT with a combination poly(I:C) (10 μg/ml) and Tri-DAP (10 μg/ml) was highly synergistic in six individuals with LTBI while a low level response was elicited in 2 of 6 individuals in the control group.

Figure 5:
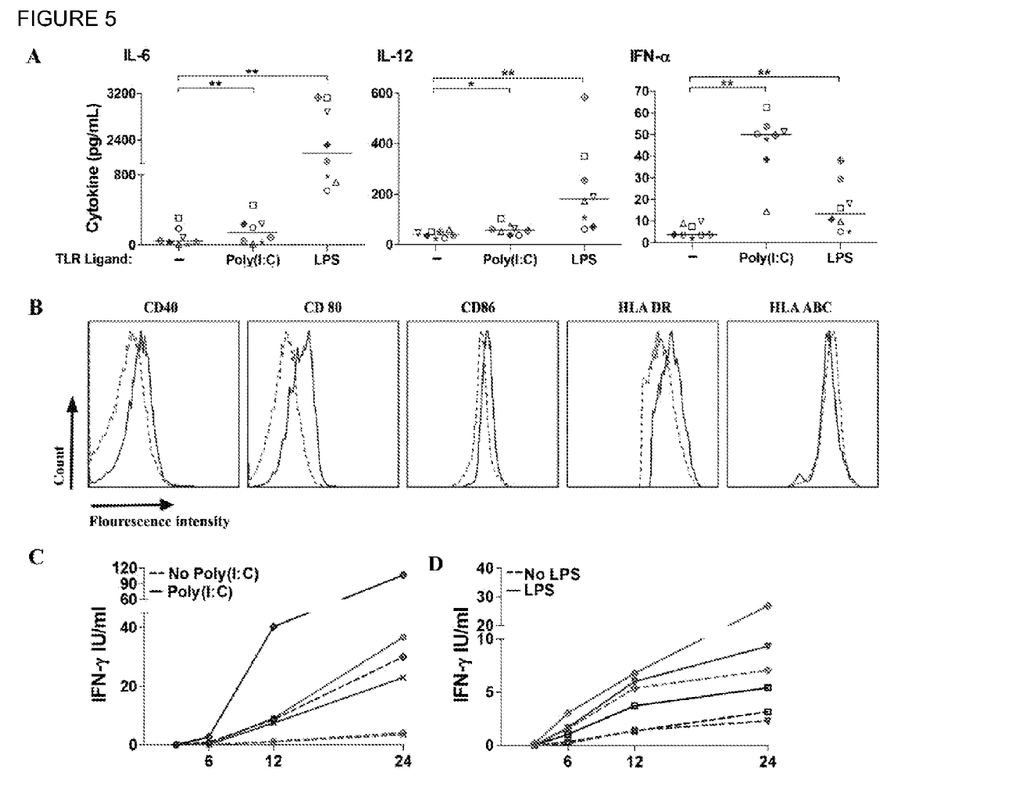
Figure 6:
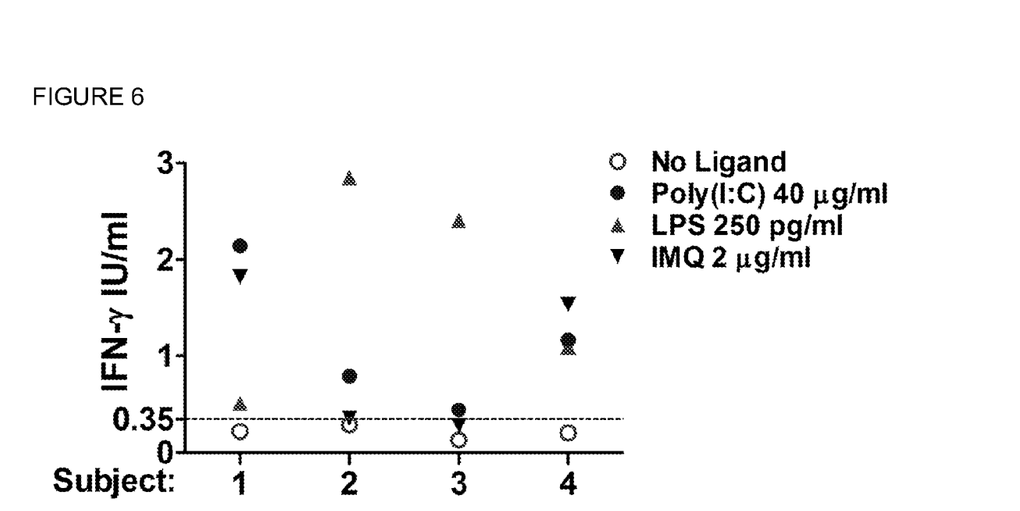
FIG. 6. Immunomodulation of Quantiferon assay unmasks a hidden IFN-γ response in subjects with LTBI. IFN-γ responses (TB Ag minus Nil) for individuals with history of LTBI (positive TST and QFT-GIT). Each individual was tested with the QFT-GIT assay in the absence or presence of poly(I:C) 40 μg/ml; LPS 250 pg/ml, and imiquimod (IMQ) 2 μg/ml. The cut-off value for the standard QFT-GIT assay (dashed line) is shown for reference. Data are representative of four of eight individuals in each group.

TLR agonists enhance markers of innate immune activation in whole blood IGRA. We hypothesized that enhancement of IFN-γ response in the whole blood IGRA by TLR agonists is mediated through the same inflammatory cytokines and type I interferons that mediate initiation of adaptive immunity in vivo. Therefore, we measured the level of 52 cytokines in the QFT-GIT Nil tube after immunomodulation with poly(I:C) and LPS. The levels of IL-6, IL-12 p40, IFN-α, and other cytokines were significantly increased after stimulation of blood cells in the Nil tube with poly(I:C) (40 μg/ml) and LPS (250 pg/ml) (FIG. 5A). However, immunomodulation of QFT-GIT assay with IL-6 at 200 and 2000 pg/ml, IL-12 at 12.5 and 25 pg/ml, and INF-α at 15 and 30 pg/ml, alone or in combination, failed to recapitulate the effects of TLR agonists on the QFT-GIT assay. To determine whether TLR agonists also enhanced the maturation of antigen presenting cells in the QFT-GIT assay, we measured the surface expression of antigen presenting molecules (MHC class I and II) and costimulatory molecules in monocytes, B cells, and dendritic cells (myeloid and plasmocytoid). Compared to unstimulated blood cells, immunomodulation with LPS (250 pg/ml) for 3 and 6 hours, but not poly(I:C) (40 μg/ml) increased the surface expression of MHC II and costimulatory molecules in monocytes and partially in B cells and myeloid dendritic cells (FIG. 5B). The induction of cytokines with poly(I:C) and LPS and the maturation of antigen presenting cells with LPS correlated with earlier and more robust release of IFN-γ (FIG. 5C).

Modulation of IGRA elicits IFN-γ responses in anergic subjects. The findings above suggest that immunomodulation of IGRA may be a useful strategy for revealing T cell responses in subjects with LTBI who otherwise do not respond to in vitro stimulation with antigens alone. To test this hypothesis, we performed the QFT-GIT assay with immunomodulation in 8 additional individuals with documented histories of LTBI but currently with negative QFT-GIT results due to spontaneous positive to negative reversions. Modulation of QFT-GIT with poly(I:C) (40 µg/ml), LPS (250 pg/ml), and imiquimod (2 µg/ml) significantly increased the IFN-γ responses in all of these individuals compared to the standard assay (FIG. 3) (P <0.05). The extent of modulation with each TLR agonist was variable in each subject; certain individuals tended to respond better to certain modulators. Overall, LPS was most consistent in eliciting a response higher than the cutoff value for the standard assay.

In this report we describe a novel application for PRR agonists as in vitro immunomodulators of IGRA for diagnosis of latent *M. tuberculosis* infection. The findings show that immunopotentiation of IGRA with PRR ligands is an effective approach for addressing the shortcomings in the sensitivity of IGRA. Immunomodulation of IGRA is particularly useful in the pediatric and immunocompromised populations where IGRAs have had lower sensitivities. In vitro immunomodulation also has a broader application for diagnosis of infectious diseases and autoimmune disorders with T cell-mediated pathogenesis.

In summary, accurate diagnostics for detection of LTBI are needed. We show that in vitro immunomodulation of IGRA with TLR agonist is a novel and practical strategy for interrogating *M. tuberculosis*-specific T cells for prior exposure to TB.

It is to be understood that this invention is not limited to the particular methodology, protocols, formulations and reagents described, as such may, of course, vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "and", and "the" include plural referents unless the context clearly dictates otherwise. Thus, for example, reference to "a complex" includes a plurality of such complexes and reference to "the formulation" includes reference to one or more formulations and equivalents thereof known to those skilled in the art, and so forth.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing, for example, the cell lines, constructs, and methodologies that are described in the publications which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

What is claimed is:

1. A method for measuring a cell mediated immune (CMI) response to a tuberculosis antigen in a subject, said method comprising:

collecting a cellular sample, comprising cells of the immune system that are capable of producing gamma interferon (IFNγ) following stimulation by antigen, from said subject;

incubating said cellular sample in vitro with a combination of tuberculosis antigen and LPS at a concentration of from 0.1 ng/ml to 100 ng/ml; and measuring the level of IFNγ produced by the cellular sample in response to the tuberculosis antigen, wherein the level of IFNγ is indicative of the capacity of said subject to mount a cell-mediated immune response against the tuberculosis antigen.

2. The method of claim 1 wherein the cellular sample is incubated with the antigen for from about 5 to about 50 hours.

3. The method of claim 1 wherein the tuberculosis antigen is ESAT-6.

4. The method of claim 1 wherein the tuberculosis antigen is CFP-10.

5. The method of claim 1 wherein the tuberculosis antigen is PPD from *Mycobacterium tuberculosis*.

6. The method of claim 1 wherein the immune effectors are detected using ELISA.

7. The method of claim 1 wherein the immune effectors are detected using ELISpot.

8. The method of claim 1, wherein said subject is immunocompromised.

* * * * *